United States Patent
Maki et al.

(10) Patent No.: US 10,888,468 B2
(45) Date of Patent: Jan. 12, 2021

(54) DISPOSABLE WEARING ARTICLE

(71) Applicant: UNICHARM CORPORATION, Shikokuchuo (JP)

(72) Inventors: Hideaki Maki, Kanonji (JP); Shunsuke Takino, Kanonji (JP); Takuya Inoue, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 275 days.

(21) Appl. No.: 15/776,896

(22) PCT Filed: Aug. 16, 2016

(86) PCT No.: PCT/JP2016/073898
§ 371 (c)(1),
(2) Date: May 17, 2018

(87) PCT Pub. No.: WO2017/085973
PCT Pub. Date: May 26, 2017

(65) Prior Publication Data
US 2018/0333311 A1    Nov. 22, 2018

(30) Foreign Application Priority Data
Nov. 20, 2015   (JP) ................................. 2015-227871

(51) Int. Cl.
 *A61F 13/49*   (2006.01)
 *A61F 13/494*   (2006.01)
 *A61F 13/53*   (2006.01)

(52) U.S. Cl.
CPC ........ *A61F 13/49012* (2013.01); *A61F 13/49* (2013.01); *A61F 13/49011* (2013.01);
(Continued)

(58) Field of Classification Search
CPC .......... A61F 13/49011; A61F 13/49012; A61F 13/4902; A61F 13/49413;
(Continued)

(56) References Cited

U.S. PATENT DOCUMENTS 5,749,865 A * 5/1998 Yamamoto ............ A61F 13/496
                                                    604/385.29
5,916,206 A * 6/1999 Otsubo ................. A61F 13/496
                                                    604/385.27
(Continued)

FOREIGN PATENT DOCUMENTS

EP     2578196 A1    4/2013
EP     2656826 A1   10/2013
(Continued)

OTHER PUBLICATIONS

International Search Report in PCT Application No. PCT/JP2016/073898, dated Oct. 18, 2016, 4pp.
(Continued)

*Primary Examiner* — Catherine L Anderson
(74) *Attorney, Agent, or Firm* — Hauptman Ham, LLP

(57) ABSTRACT

The present invention provides a disposable wearing article which prevents a position shift of a front waist region without a part of a front waist region receding in a concave portion of the abdomen of the wearer. A plurality of linear front waist elastics contractible in a lateral direction is disposed in a front waist region of a disposable wearing article. The front waist elastics have (include) a first elastic positioned adjacent to an outer side of a front-end edge of a liquid absorbent core in a vertical direction, a second elastic positioned adjacent to an inner side of the front-end edge in the vertical direction, and a third elastic positioned adjacent to an inner side of the second elastic in the vertical direction.
(Continued)

A contractile force of the first elastic and the second elastic is weaker than a contractile force of the third elastic.

7 Claims, 8 Drawing Sheets

(52) U.S. Cl.
CPC .. *A61F 13/49019* (2013.01); *A61F 13/49413* (2013.01); *A61F 13/49466* (2013.01); *A61F 13/53* (2013.01); *A61F 2013/49028* (2013.01); *A61F 2013/4948* (2013.01); *A61F 2013/49092* (2013.01)

(58) Field of Classification Search
CPC .. A61F 2013/15284; A61F 2013/15325; A61F 2013/49025; A61F 2013/49026; A61F 2013/49028; A61F 2013/49031; A61F 2013/49092
See application file for complete search history.

(56) References Cited

U.S. PATENT DOCUMENTS

| | | | | |
|---|---|---|---|---|
| 8,282,617 | B2 * | 10/2012 | Kaneda | A61F 13/49011 604/393 |
| 8,518,010 | B2 * | 8/2013 | Kuwano | A61F 13/49011 604/385.3 |
| 9,023,007 | B2 * | 5/2015 | Hashino | A61F 13/49406 604/385.24 |
| 9,039,669 | B1 * | 5/2015 | Lavon | A61F 13/49012 604/385.29 |
| 2011/0106039 | A1 | 5/2011 | Saito et al. | |
| 2012/0289921 | A1 | 11/2012 | Hashino et al. | |

FOREIGN PATENT DOCUMENTS

| | | |
|---|---|---|
| JP | 2009-240694 A | 10/2009 |
| JP | 2011-136082 A | 7/2011 |
| JP | 2012-157476 A | 8/2012 |
| WO | 2014/192981 A1 | 12/2014 |
| WO | 2015/001915 A1 | 1/2015 |

OTHER PUBLICATIONS

Extended European Search Report in EP Application No. 16865976.1, dated Oct. 10, 2018, 6pp.

* cited by examiner

DISPOSABLE WEARING ARTICLE

RELATED APPLICATIONS

The present application is a National Phase of PCT/JP2016/073898, filed Aug. 16, 2016, and claims priority to Japanese Patent Application No. 2015-227871, filed Nov. 20, 2015.

TECHNICAL FIELD

The present disclosure relates to a disposable wearing article such as a disposable diaper, disposable toilet training pants, disposable incontinence pants, and disposable sanitary pants.

BACKGROUND

Conventionally, disposable wearing articles having an elastic area in a front waist region are known. For example, Patent Literature 1 discloses a disposable wearing article including an elastic waist panel having front and rear waist panels, and an absorbent panel joined to the elastic waist panel, and in which a plurality of front and rear waist elastic members extending in a lateral direction are disposed in the waist panel. The absorbent panel includes a liquid absorbent core, and a front and rear ends extending outboard in a vertical direction from front and rear end edges of the liquid absorbent core.

CITATION LIST

Patent Literature

[Patent Literature 1]: Japanese Patent Application Laid-open Publication No. 2009-240694

SUMMARY

Technical Problem

In the disposable wearing article disclosed in Patent Literature 1, the front waist region has an outer elastic area extending in the lateral direction along a waist opening edge, an inner elastic area extending to be intersecting the liquid absorbent core, and an intermediate elastic area positioned in the inner elastic area and overlapping with a front-end part of the absorbent panel, and a tensile stress of the intermediate elastic area is higher than a tensile stress of other elastic areas. This makes it possible to fit the front end having a relatively low stiffness and including no liquid absorbent core stably to the body of a wearer.

However, when the wearer is a young baby, a portion of the body put in contact with the intermediate elastic area extending downward to be inclined below from the middle of an abdomen bulged frontward and most concave in the abdomen, when the wearer bends forward, the front end having relatively low stiffness and large contracted dimension is pressed against the abdomen and is apt to move downward and the waist opening edge may slip downward thereby causing leakage of body exudates.

An object of the present invention is to provide a disposable wearing article in which a position shift of the front waist region is prevented by fitting the front waist region stably to a concave portion of the abdomen of the wearer.

Solution to Problem

The present invention is directed to a disposable wearing article having a vertical direction and a lateral direction, including a front waist region, a rear waist region, a crotch region extending between the front waist region and the rear waist region, and an absorbent panel having a liquid absorbent core extending to the front waist region and the rear waist region centering on the crotch region.

In the disposable wearing article according to the present invention, a plurality of linear front waist elastic members contractible in the lateral direction is disposed in the front waist region, and the front waist elastic members include a first elastic member positioned adjacent to an outer side of a front end edge of the liquid absorbent core in the vertical direction, a second elastic member positioned adjacent to an inner side of the front end edge in the vertical direction, and a third elastic member positioned adjacent to an inner side of the second elastic member in the vertical direction, and a contractile force of the first elastic member and the second elastic member is weaker than a contractile force of the third elastic member.

In the front waist elastic members of the front waist region, an elongation rate of the first elastic member is lower than an elongation rate of the second and third elastic members. With such embodiment, suppressing the elongation rate of the first elastic member which is relatively more susceptible to be elongated, and not overlapping the liquid absorbent core, it is possible to elongate a vicinity of the front end edge of the liquid absorbent core in a balanced manner.

A spaced-apart dimension between the front end edge of the liquid absorbent core and the first elastic in the vertical direction is larger than a spaced-apart dimension between the front-end edge and the second elastic member in the vertical direction. With such embodiment, it is possible to fit stably to the body of a wearer at a portion overlapping with the liquid absorbent core.

The front elastic area has an inner end edge, an outer end edge, an outer elastic area positioned on the outer end edge, an inner elastic area positioned on the inner end edge, a first intermediate elastic area adjacent to an inner side of the outer elastic area in the vertical direction, including the first elastic and the second elastic, and a second intermediate elastic area positioned between the first intermediate elastic area and the inner elastic area, including the third elastic member, and a tensile stress of the first intermediate elastic area is higher than a tensile stress of the outer elastic area. With such embodiment, it is easy to widen the waist opening at the time of wearing on one hand while it is possible to hold the front waist region firmly in a worn state.

In the front waist region, a correlation for tensile stress of elastic areas is a tensile stress of the second intermediate elastic area>the tensile stress of the first intermediate elastic area≥a tensile stress of the outer elastic area>a tensile stress of the inner elastic area, the tensile stress of the second intermediate elastic area is the maximum in the front elastic area. With such embodiment, it is possible to fit the front waist region stably to the most concave portion of the abdomen of the wearer.

A contractile force of elastic member in the first intermediate elastic area, excluding the first and the second elastic members is stronger than a contractile force of the first and second elastic members, it does not create an uncomfortable feeling by pressing strongly against the wearer's body in the vicinity of the front end edge of the liquid absorbent core while it exerts the necessary tensile stress as overall second intermediate elastic area. With such embodiment, it is possible to prevent effectively the position shift of the front waist region.

The rear waist region has an inner end edge, an outer end edge, an outer elastic area positioned on the outer end edge, an inner elastic area positioned on the inner end edge, a first intermediate elastic area adjacent to an inner side of the outer elastic area in the vertical direction, and a second intermediate elastic area positioned between the first intermediate elastic area and the inner elastic area, and a correlation for tensile stress of elastic areas is a tensile stress of the outer elastic area≥a tensile stress of the first intermediate elastic area>a tensile stress of the second intermediate elastic area>a tensile stress of the inner elastic area, in the rear waist region. With such embodiment, it is possible to hold firmly on the wearer's body on the waist opening side.

The tensile stress of the outer elastic area of the rear waist region being higher than a tensile stress of the outer elastic area of the front waist region. With such embodiment, it is possible to fit the disposable wearing article to the body at a rear side having a lesser movement compared to an abdomen side, and the waist opening edge part is capable of exerting the necessary holding force around the waist.

The first intermediate elastic area of the front waist region and the first intermediate elastic area of the rear waist region overlap in planar view with the front end edge positioned outboard of the front end edge of the liquid absorbent core in the absorbent panel in the vertical direction and the rear end edge positioned outboard of the rear end edge of the liquid absorbent core in the absorbent panel in the vertical direction respectively.

The disposable wearing article further includes a pair of leakage barrier cuffs extending in the vertical direction on a skin facing surface of the absorbent panel, and the leakage barrier cuff has both end fixing parts opposed to each other in the vertical direction, both side extending in the vertical direction, and a free edge in which cuff elastic members extending in the vertical direction is disposed, and both end fixing parts are fixed at the front end edge and the rear end edge of the absorbent panel. With such embodiment, a thickness of the front and rear end edges of the absorbent panel is partially large, and even when an elastic member having a relatively stronger contractile force is disposed to overlap (the front and rear end edges), no pressure marks are left on the wearer's body.

A deformation guiding part extending inward in the vertical direction from the front end edge is formed in the liquid absorbent core. With such embodiment, it is possible to deform the front end edge of the liquid absorbent core along the abdomen by an action of the front waist elastic.

Advantageous Effects of Invention

According to a disposable wearing articles according to one or more than one embodiments of the present invention, it is possible to prevent part of the front waist region from moving downward at a concave portion of the abdomen by pressing the liquid absorbent core against the wearer's body, without creating an uncomfortable feeling against the wearer by tightening hard the area near the front end edge of the liquid absorbent core.

DESCRIPTION OF EMBODIMENTS

The embodiments described below relate to a disposable diaper 10 illustrated in FIGS. 1 through 8, which is an example of the present invention, and include both optional and preferred features as well as those features which are essential of the invention. In FIGS. 2, 3, 4, and 8, the diaper 10 is in a state of being elongated to the extent such that, gathers by elastics have disappeared practically by a natural visual perception against a contractile force of each elastic member that will be described later. In each diagram, for illustrating as to how front and rear waist elastic members 30, 40 to be described later are disposed, the diaper 10, even when viewed from a skin facing side, is shown by virtual lines.

First Embodiment

Figure 1:
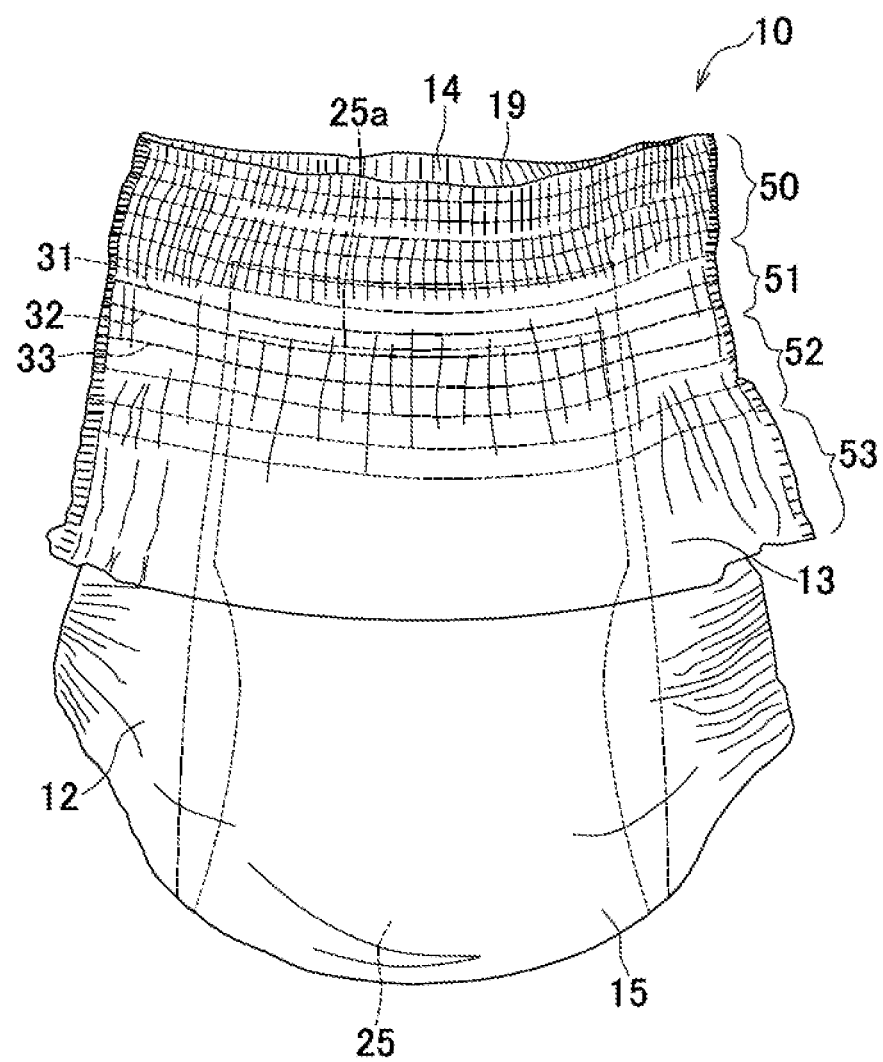
FIG. 1 is a perspective view illustrating a disposable diaper as an example of a disposable wearing article according to a first embodiment of the present invention.
Figure 2:
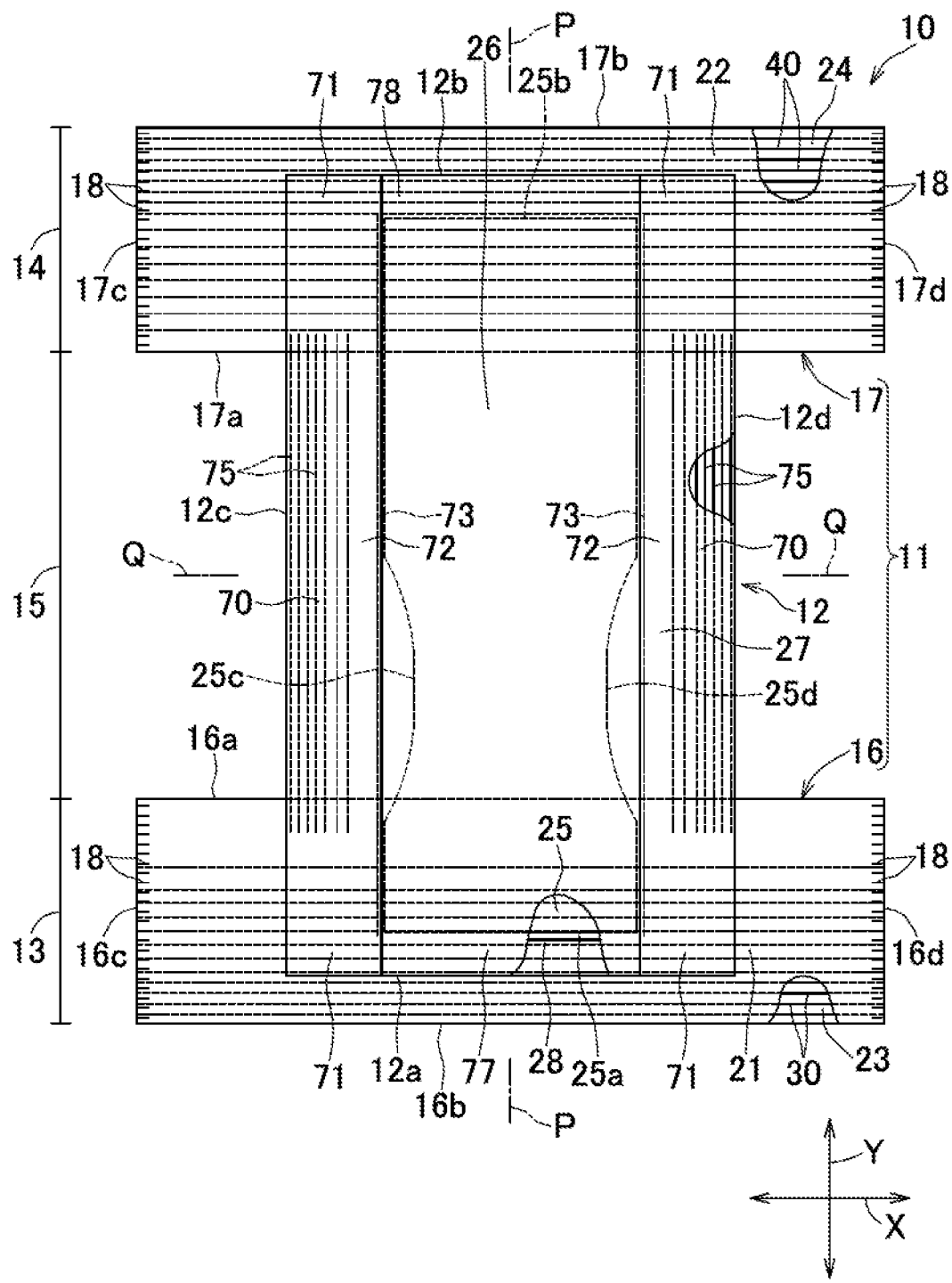
FIG. 2 is a partially cutaway plan view showing an unfolded state when a side seam of the disposable diaper is peeled off and extended in a frontward-rearward direction, as seen from an inner surface thereof.
Figure 3:
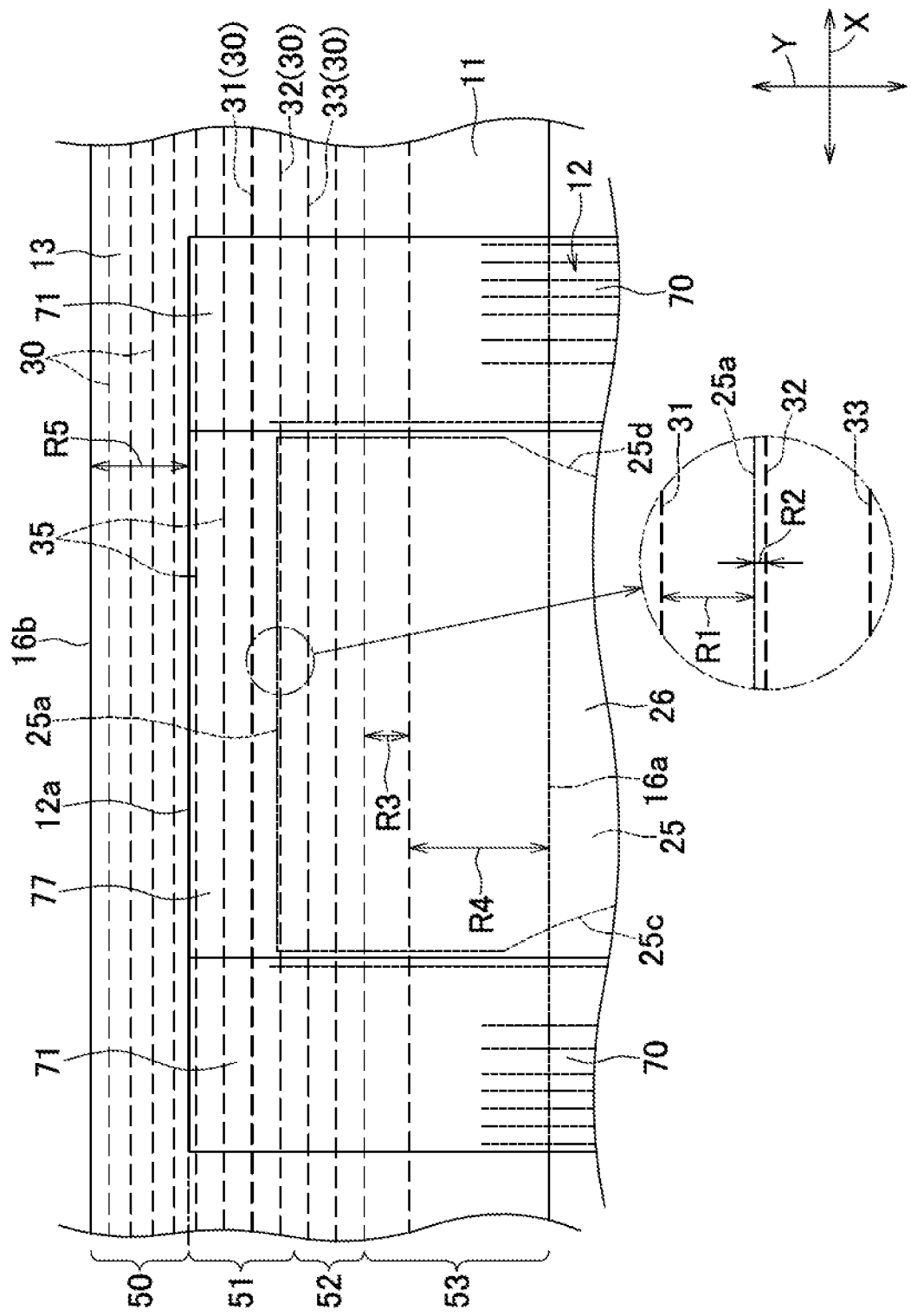
FIG. 3 is an enlarged view of a front waist region.

As shown in FIG. 1 to FIG. 3, the disposable diaper 10 shown as an example of a disposable wearing article of the present invention has a vertical direction Y and a lateral direction X, a virtual center line P-P bisecting a width dimension in the lateral direction X, a skin facing surface and a non-skin facing surface opposite to the skin facing surface, and includes an elastic waist panel 11, an absorbent panel 12 fixed to a skin facing surface of the elastic waist panel 11, a front waist region 13, a rear waist region 14, and a crotch region 15 extending in the vertical direction Y between the front and rear waist regions 13, 14. The diaper is symmetrical about the virtual center line P-P, and the elastic waist panel 11 includes a front waist panel 16 defining the front waist region 13, and a rear waist panel 17 defining the rear waist region 14.

The front waist panel 16 is defined to be oblong rectangular shaped by an inner end edge (inner end edge of the front waist region 13) 16a extending in the lateral direction X and intersecting the absorbent panel 12, an outer end edge (outer end edge of the front waist region 13) 16b extending in the lateral direction X, and side edges (side edges of the front waist region 13) 16c, 16d extending in the vertical direction Y.

The rear waist panel 17 has almost the same shape and size as of the front waist panel 16, and is defined to be oblong rectangular-shaped by an inner end edge (inner end edge of the rear waist region 14) 17a extending in the lateral direction X and intersecting the absorbent panel 12, an outer end edge (outer end edge of the rear waist region 14) 17b extending in the lateral direction X, and side edges (side edges of the rear waist region 14) 17c, 17d extending in the vertical direction Y.

Both side edges of the front waist panel 16 and both side edges of the rear waist panel 17 are overlapped with each other, and are joined by side seams 18 continually in the vertical direction Y, and a waist opening 19 and a pair of leg openings are defined (see FIG. 1). The side seam 18 is made by a well-known joining means such as various thermal welding means, for example, heat embossing/debossing, and ultrasonic processing.

The front and rear waist panels 16, 17 include inner layer sheets 21, 22 on the skin facing surface, and outer layer sheets 23, 24 on the non-skin facing surface. The inner layer sheets 21, 22 and the outer layer sheets 23, 24 are formed of liquid non-permeable materials having a mass in a range of 15 to 30 g/cm$^2$, such as SMS (spun-bonded/melt-blown/spun-bonded) fibrous nonwoven fabrics or spun-bonded fibrous nonwoven fabrics, or plastic sheets, and laminated sheets thereof. Both pairs of sheets 21 to 24 are joined by hot-melt adhesives (not shown) applied to an inner surface of at least one of the sheets.

In the front and rear waist panels 16, 17, between the inner layer sheets 21, 22 and the outer-layer sheets 23, 24, a plurality of linear waist elastic members 30, 40 extending in the lateral direction X between the side edges 16c, 16d, 17c, and 17d is fixed contractively under tension in the lateral direction X by a well-known adhesive means such as hot-melt adhesive. The inner and outer layer sheets 21 to 24 may be jointed to each other with hot-melt adhesives for example applied to each of the elastic members forming the front and rear waist elastic members 30, 40.

Figure 4:
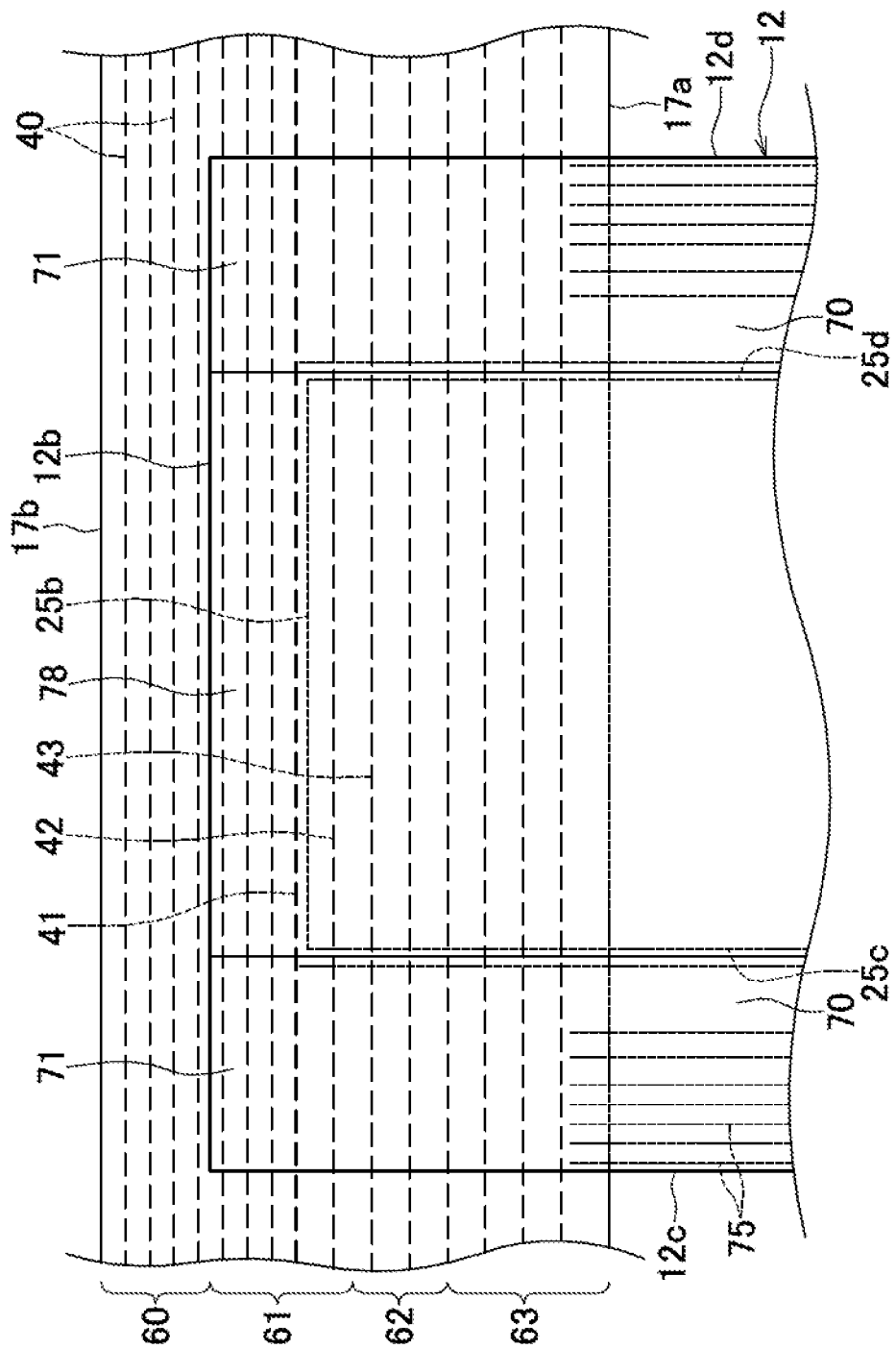
FIG. 4 is an enlarged view of a rear waist region.

Referring to FIG. 2 to FIG. 4, the plurality of linear front and rear waist elastics 30, 40 are disposed in the front and rear waist regions 13, 14, and have front and rear waist elastic areas contractible in the lateral direction X between the side edges 16c, 16d, 17c, and 17d. The front and rear waist elastic members include outer elastic areas 50, 60 extending in the lateral direction X and positioned on the outer-end edges 16b, 17b, inner elastic areas 53, 63 extending in the lateral direction and positioned on the inner-end edges 16a, 17a side, first intermediate elastic areas 51, 61 extending in the lateral direction X, adjacent to an inner side of the outer elastic areas 50, 60 in the vertical direction Y, and second intermediate elastic areas 52, 62 extending in the lateral direction X and positioned between the inner elastic areas 53, 63 and the first intermediate elastic areas 51, 61. The front and rear waist elastic members 13, 14, by being disposed in these elastic areas, have elasticity at least in the lateral direction as a whole, and a plurality of gathers is formed in an unworn state (contracted state). In order to avoid the formation of gathers inhibiting liquid absorbency on the liquid absorbent core 25 due to a contractile force of the front and rear waist elastic members 30, 40, the front and rear waist elastic members 30, 40 may be cut or removed in an area where the liquid absorbent core 25 are present. However, even in this instance, as the contractile force of the front and rear waist elastics 30, 40 is exerted in an area of the front and rear waist regions 13, 14 from the side edges 16c, 16d, 17c, 17d to side edges of the liquid absorbent core 25, the liquid absorbent core is not spaced apart from the wearer's body.

The absorbent panel 12 has a vertically long rectangular shape defined by front and rear end edges 12a, 12b, and side edges 12c, 12d extending in the vertical direction Y between the front and rear end edges 12a, 12b. The absorbent panel 12 includes the liquid absorbent core 25 wrapped in a liquid diffusion core cover sheet, a hydrophilic/liquid permeable inner surface sheet (body side liner) 26 positioned on a skin facing surface side of the liquid absorbent core 25, a covering sheet 27 formed of a hydrophobic or liquid impermeable fibrous nonwoven fabric positioned at a non-skin facing surface of the liquid absorbent core 25, and a leakage barrier film 28 formed of a hydrophobic or liquid impermeable plastic sheet having a size covering at least the bottom surface thereof, on the non-skin facing surface of the liquid absorbent core 25.

The liquid absorbent core 25 is a semi-rigid panel formed to have a required shape by mixing superabsorbent polymer particles (SAP) and fluff wood pulp, and has an outer contour defined by front and rear end edges 25a, 25b, and two edges 25c, 25d extended concavely in the vertical direction Y between the front and rear end edges 25a, 25b. Moreover, the core cover sheet is a sheet for diffusing body fluids and retaining shape of the liquid absorbent core 25, and is formed of a relatively thin material such as hydrophilic sheet and tissue paper.

The covering sheet 27 has two side parts 70 positioned outboard in the lateral direction X from both edges of the leakage barrier film 28. Both side parts 70 are folded inward along both edges of the inner surface sheet 26, and have two fixing side parts (proximal parts) fixed to the inner surface sheet 26 extending in the vertical direction Y along folding site, and two end fixing parts 71 by which an inner surface of both end parts are fixed to the inner-surface sheet. A sleeve or loop-like free edge part (distal edge) 72 not fixed to an inner surface of the inner surface sheet 26 is positioned on outer edges of both side parts 70, and a linear cuff elastic member 73 extended in the vertical direction Y is secured contractively under tension to an interior of the free edge 72. By the cuff elastic member 73 being contracted, the free edge 72 is spaced away from the inner surface sheet toward the body side of the wearer, and both side parts 70 function as barrier cuffs sealing off the body exudates by fitting to the thighs of the wearer. Moreover, linear leg elastic members 75 is secured contractively under tension in the vertical direction Y, between both side parts 70 of the covering sheet 27 and the leakage barrier film 28. In a planar view of the diaper 10, front and rear ends of the leg elastic members 75 are positioned to be overlapping with the front and rear waist panels 16, 17. In such manner, by a leg elastic area and a portion of the front and rear waist elastic areas intersecting due to the contraction effect of the leg elastic members 75, a virtual elastic belt is formed in a leg opening edge, and it is possible to fit stably in surface contact with the body of the wearer, and it is possible to prevent the leakage of body exudates.

Referring again to FIG. 3 and FIG. 4, to describe further specifically about each elastic area in the front and rear waist regions 13, 14 on the basis of a positional relationship with the absorbent panel 12, the outer elastic areas 50, 60 are positioned between the outer end edges 16b, 17b of the front and rear waist regions 13, 14 and front and rear end edges 12a, 12b of the absorbent panel 12, and the first intermediate elastic areas 51, 61 are positioned to be overlapping with front and rear end parts 77, 78 positioned outboard from the front and rear end edges 25a, 25b of the liquid absorbent core 25 in the vertical direction Y in the absorbent panel 12. Moreover, in the front waist elastic area, a boundary of the first intermediate elastic area 51 and the second intermediate elastic area 52 is a middle part of a portion at which a second elastic member 32 and a third elastic member 33 that will be described later, extending to intersect the liquid absorbent core 25 are spaced apart. A boundary of the second intermediate elastic areas 52, 62 and the inner elastic areas 53, 63 is not regulated clearly, and can be divided by bisecting an area extending downward from the first intermediate elastic areas 51, 61 of the front waist region 13. Moreover, although it is also possible to define each elastic area by dividing a dimension of the front and rear waist regions 13, 14 in the vertical direction Y equally into four parts, even in that instance, the boundaries of the first intermediate elastic areas 51, 61 and the second intermediate elastic areas 52, 62 either overlap with the front and rear end edges 25a, 25b of the liquid absorbent core 25 or are positioned in the vicinity thereof.

Referring to FIG. 3, the front waist elastic 30 includes a first elastic member 31 positioned adjacent to an outer side of the front end edge 25a of the liquid absorbent core 25 in the vertical direction Y, a second elastic member 32 positioned adjacent to an inner side of the front end edge 25a in the vertical direction Y, and a third elastic member 33 positioned adjacent to an inner side of the second elastic member 32 in the vertical direction Y. The first elastic member 31 and the second elastic member 32 are positioned opposed to each other sandwiching a front end edge of the liquid absorbent core 25.

Figure 5:
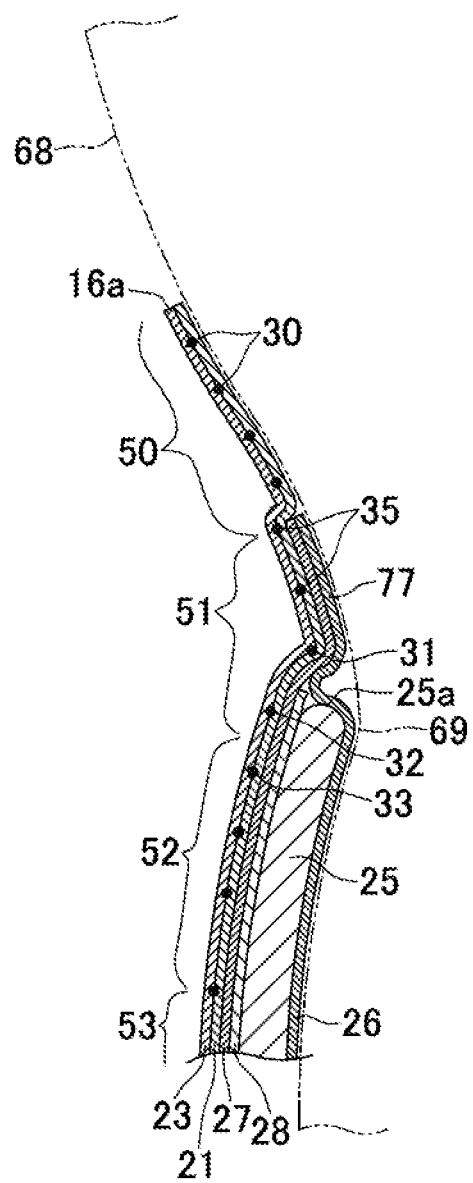
FIG. 5 is a side view showing the (disposable) diaper in a worn state.

Referring to FIG. 5, in the worn state of the diaper 10, the front end part of the liquid absorbent core 25 is positioned opposed to each other with a portion 69 which is the most concave portion of the abdomen, extending to be inclined downward from the middle of the abdomen of the wearer, bulged frontward. The liquid absorbent core 25 being semi-rigid, has a relatively high rigidity, and is required to be brought into a stable contact so that a portion near the front end edge 25a is not spaced apart from the wearer's body. However, when a tensile stress of an overall portion of the front waist elastic area overlapping with the front end edge part of the liquid absorbent core 25 is made high, the portion near the front end edge 25a bites into the wearer's body, and there may arise an unevenness with the front end edge part 77 of the absorbent panel 12 having a relatively lower stiffness being formed only by a sheet member, and the waist opening edge may slip down.

In the present embodiment, a contractile force of the first and second elastics 31, 32 adjacent to the outer side and the inner side of the front end edge 25a of the liquid absorbent core 25 being relatively weaker, there is no unevenness occurring between the front end edge 25a and the front end part 77 by the portion near the front end edge 25a of the liquid absorbent core 25 pressing against the body. Moreover, a contractile force of the third elastic member 33 adjacent to the second elastic member 32 being stronger than the contractile force of the first and second elastic members 31, 32, the front end edge part of the liquid absorbent core 25 is pressed against the portion 69 which is the most concave portion of the abdomen in the wearer's body, and it is possible to prevent it from being lifting-off.

Regarding the contractile force of the first to third elastic members 31 to 33, the contractile force of the first elastic member 31 is in a range of 0.12 N to 0.15 N, the contractile force of the second elastic member 32 is in a range of 0.16 N to 0.20 N, and the contractile force of the third elastic member 33 is in a range of 0.21 N to 0.26 N, and in a specific example, the contractile force of the first elastic member 31 is 0.133 N, the contractile force of the second elastic member 32 is 0.178 N, and the contractile force of the third elastic member 33 is 0.234 N.

<Method for Measuring Contractile Force of Elastic Member>

Contractile force of the front and rear waist elastic members 30, 40 including the first to third elastic members 31 to 33 can be calculated by cutting off an area including each elastic member in the front and rear waist panels 16, 17 having a predetermined width (dimension in the vertical direction Y) in the form of a strip specimen. More specifically, at the time of measuring the contractile force of the second elastic 32 for example, first, after the absorbent panel 12 was extracted from the elastic waist panel 11, the side seam 18 was peeled off, and the front and rear waist panels 16, 17 were separated. Next, for the front waist panel 16, the strip specimen of a predetermined width extending between both side edges 16c, 16d including the second elastic member 32 was cut out along a first cutting line intersecting a middle part bisecting a dimension between the pitch of the first elastic member 31 and the second elastic member 32 in the vertical direction Y and a second cutting line intersecting a middle part (site) bisecting a dimension between the pitch of the second elastic member 32 and the third elastic member 33 in the vertical direction Y, and let to be a test specimen. Before cutting out the test specimen, the diaper 10 was unfolded, and a dimension in the lateral direction X of the test specimen was measured in a state of the unfolded diaper 10 elongated (stretched) to an extent such that gathers by contraction effect of each elastic member disappeared from a surface of the unfolded diaper 10, and the dimension measured was let to be an initial dimension.

Next, by using Autograph type tensile tester (such as AG-1KN1) manufactured by Shimadzu Seisakusho Co., Ltd. (Shimadzu Corporation), one end of each sample was pinched in a fixed chuck and the other end thereof was pinched in a movable chuck, and upon turning over after elongating to approximately 90% size of the initial dimension at a velocity of 300 mm/min, a tensile load (N) when made to contract to 75% size of the initial dimension was calculated, and was let to be the contractile force of each of the elastic members 30, 40.

It is possible to adjust appropriately the contractile force of each of the elastic members 30, 40 according to a fineness and elongation rate, and with regard to a thickness of the first to third elastic members 31 to 33, the thickness of the first and second elastic members 31, 32 is in a range of 350 dtex to 550 dtex, and the thickness of the third elastic member 33 is in a range of 500 dtex to 700 dtex. Moreover, the first elastic member 31 is fixed in a state of being elongated 2.1 to 2.4 times, and the second and third elastic members 32, 33 are secured in a state of being elongated 2.4 to 2.6 times, and the elongation rate of the first elastic member 31 is lower than the elongation rate of the second and third elastic members 32, 33. Since the first elastic 31, unlike the second and third elastic members 32, 33, does not intersect the liquid absorbent core 25, is susceptible to be elongated relatively easily, and when the elongation rate thereof is relatively higher, the first elastic member 31 is widened in a direction around the waist by the abdomen bulging frontward, whereas, since the elastic member is hard to be elongated at a portion in which the liquid absorbent core 25 is disposed, sometimes a gap may be developed in between. In the present embodiment, by setting the elongation rate of the first elastic member 31 to be lower than the elongation rate of the second and third elastic members 32, 33, by making elongate in a balanced manner by reducing a difference in an amount of elongation of the elastic members, the abovementioned disadvantage is avoided.

Referring to FIG. 3, a spaced-apart dimension R1 in the vertical direction Y between the front end edge 25a of the liquid absorbent core 15 and the first elastic member 31 is larger than a spaced-apart dimension R2 in the vertical direction between the front end edge 25a and the second elastic 32. More specifically, the spaced-apart dimension R1 is in a range of 4.0 mm to 6.0 mm, whereas, the spaced-apart dimension R2 is in a range of 0.5 mm to 1.5 mm. In such manner, by bringing the second elastic member 32 intersecting the liquid absorbent core 25 closer to the front end edge 25a than the first elastic member 31, it is possible to press the front-end edge part of the liquid absorbent core 25 against the wearer's body, and to suppress it from being spaced apart from the body. Regarding a spaced-apart dimension (pitch) in the vertical direction Y between the front waist elastic members 30, the pitch of the front waist elastic members 30 disposed in the outer elastic area 50 is in a range of 3.0 mm to 6.0 mm, the pitch of the front waist elastic members 30 in the first and second intermediate elastic areas 51, 52 including the first to third elastic members 31 to 33 is in a range of 4.0 mm to 7.0 mm, and the pitch of the elastics of the outer elastic area 50 is smaller than the pitch of the elastic members of the first and second intermediate elastic areas 51, 52.

A spaced-apart dimension R3 between an elastic member positioned in the inner elastic area 53 and an elastic member positioned at a lowermost position in the second intermediate elastic area 52 is in a range of 8.0 mm to 12.0 mm, and a spaced-apart dimension R4 between an elastic member positioned in the inner elastic area 53 and the inner-end edge 16a of the front waist region 13 is in a range of 28 mm to 35 mm. Moreover, a spaced-apart dimension R5 from an outer end edge 16b of the front waist elastic 13 to the front end edge 12a of the absorbent panel 12 is in a range of 20 mm to 24 mm.

In the front waist elastic area, the first and second elastic members 31, 32 are positioned in the first intermediate elastic area 51, and the third elastic member 33 is positioned in the second intermediate elastic area 52. Moreover, a tensile stress of a predetermined width in the lateral direction X of the first intermediate elastic area 51 is higher than a tensile stress of a predetermined width in the lateral direction X of the outer elastic area 50. The first intermediate elastic area 51 overlaps with the absorbent panel 12, and the number of members layered in the first intermediate elastic area 51 is large, and it is hard to stretch. Therefore, by setting the tensile stress of the first intermediate elastic area 51 to be higher than the tensile stress of the outer elastic area 50, at the time of wearing, it is possible to widen in the lateral direction X together with the outer elastic area 50.

In the front waist elastic area, a correlation of tensile stress of a predetermined width in the lateral direction X of elastic areas is, the tensile stress of the second intermediate elastic area 52>the tensile stress of the first intermediate elastic area 51≥the tensile stress of the outer elastic area 50>the tensile stress of the inner elastic area 53.

Figure 6A:
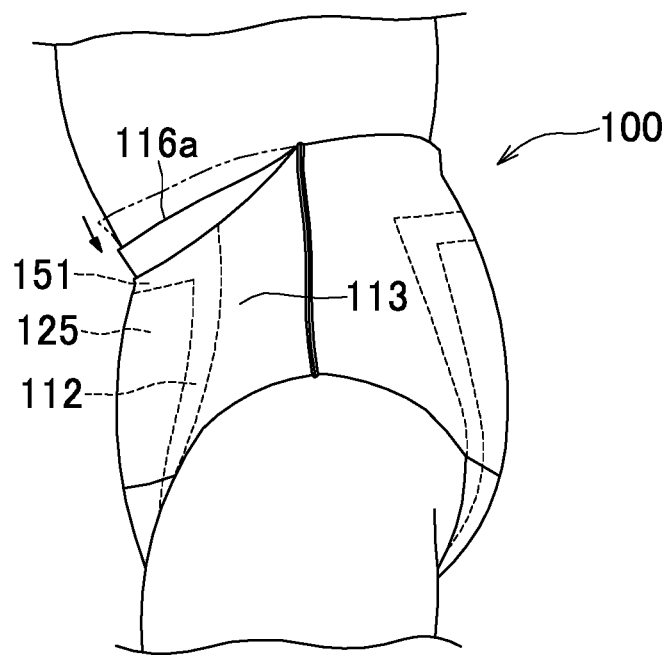
FIG. 6A is a diagram showing a disposable diaper of an example for comparison, in a worn state.

FIG. 6A is a diagram showing a worn state when the tensile stress of a first intermediate area 151 in the front waist elastic area is set to be the maximum in a diaper 100 in an example for comparison having a basic arrangement similar to that of the diaper 10. In a front waist elastic area 113, when a tensile stress of the first intermediate elastic area 151 is let to be the maximum, since the first intermediate elastic area 151 is at a position facing the most concave portion of the abdomen extended to be inclined downward from the middle of the abdomen of the wearer, and an amount of contraction is even larger, and there is an unevenness between the first intermediate elastic area 151 and a liquid absorbent core 125 having a relatively higher stiffness, and the first intermediate elastic area 151 is receded between the liquid absorbent core 125 of an absorbent panel 112 and the wearer's body, and the front waist opening edge 116a is inclined downward, which sometimes leads to a downward shift in position of the overall front waist region.

Figure 6B:
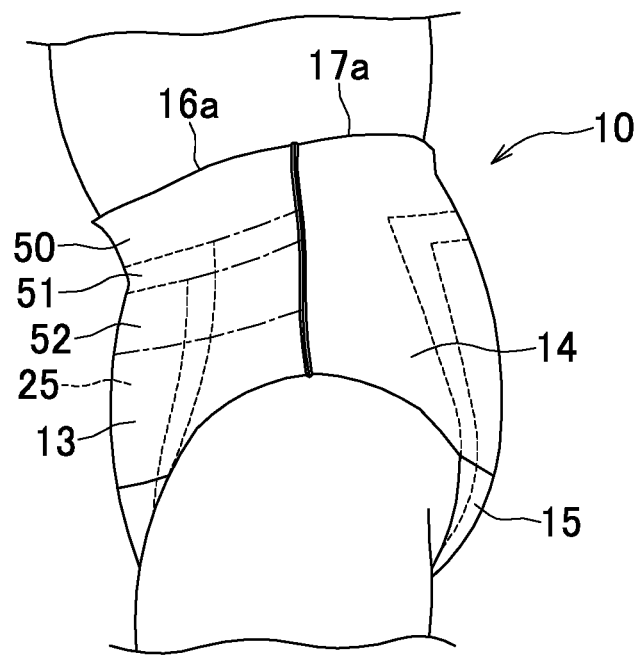
FIG. 6B is a diagram showing a disposable diaper of an example, in a worn state.

FIG. 6B is a diagram showing a worn state of the diaper 10 in an example, and by setting the tensile stress of the second intermediate elastic area 52 overlapping with the front end edge part of the liquid absorbent core 25 to be the maximum, the liquid absorbent core 25 is pressed firmly against the wearer's body, and a position shift of the overall front waist region 13 is suppressed, and the first intermediate elastic area 51 is not receded in a concave portion of the abdomen.

A tensile stress of a predetermined width in the lateral direction of the front waist elastic area is specifically in a range of 0.019 N/mm to 0.029 N/mm for the outer elastic area 50, 0.02 N/mm to 0.03 N/mm for the first intermediate elastic area 51, 0.023 N/mm to 0.033 N/m for the second intermediate elastic area 52, and 0.019 N/mm to 0.029 N/mm for the inner elastic area 53.

Moreover, in the first intermediate elastic area 51, a contractile force of a plurality of elastic members (elastic members positioned outboard of the first elastic member 31 in the vertical direction Y) excluding the first and second elastic members 31, 32 is stronger than a contractile force of the first and second elastic members. More specifically, an elastic member 35 has a thickness almost the same as that of the third elastic member 33, which is in a range of 500 dtex to 700 dtex, and the first elastic member 31 is secured in a state of being elongated 2.1 to 2.4 times. By disposing the elastic member 35 that may exert a relatively stronger contractile force at a location where an unevenness is susceptible to be formed due to a change in the sheet members that are layered, even near the front end edge 12a of the absorbent panel 12, it is possible to suppress an occurrence of the unevenness. Moreover, a fixing part 71 of the leakage barrier cuff of the covering sheet 27 is positioned on the front end part 77 of the absorbent panel 12. By the fixing part 71 being positioned on the front end part 77, the front end part 77 becomes a relatively thicker part, even when the elastic member 35 having a relatively stronger contractile force is disposed, no pressure marks are left on the wearer's body.

Referring again to FIG. 4, in the rear waist elastic area, elastic members equivalent to the first to third elastic members 31 to 33 of the front waist elastic area, or in other words, elastic members 41, 42 positioned inboard and outboard of the rear end edge 25b of the liquid absorbent core 25 in the vertical direction Y, and an elastic member 43 positioned inboard of the elastic 42 in the vertical direction Y have the same thickness and elongation rate, and more specifically, have thickness in a range of 500 dtex to 700 dtex, and are secured in a state of being elongated 2.4 to 2.6 times. In such manner, by setting the thickness and the elongation rate of the elastic members 41 to 43 to be the same as the thickness and the elongation rate of the third elastic member 33 of the front waist elastic area, it is possible to press a rear-end edge part of the liquid absorbent core 25 against the body with a relatively stronger contractile force. The rear-end edge part of the liquid absorbent core 25 being positioned facing the hip portion protruding rearward, even when pressed relatively strongly against the hip portion, there is no unevenness formed between the rear end edge part and the rear end part 78 of the absorbent panel 12, as in the front end edge part of the liquid absorbent core 25.

In the rear waist elastic area, a correlation of tensile stress of elastic areas is a tensile stress of the outer elastic area 60≥a tensile stress of the first intermediate elastic area 61>a tensile stress of the second intermediate elastic area 62>a tensile stress of the inner elastic area 63. In such manner, unlike the front waist elastic area, by letting the tensile stress of the outer elastic area 60 to be the maximum in the rear waist elastic area, it is possible to bring the rear waist opening edge part in a stable contact with a dorsal surface of the wearer, and to prevent a position shift of the rear waist region 14.

Figure 7:
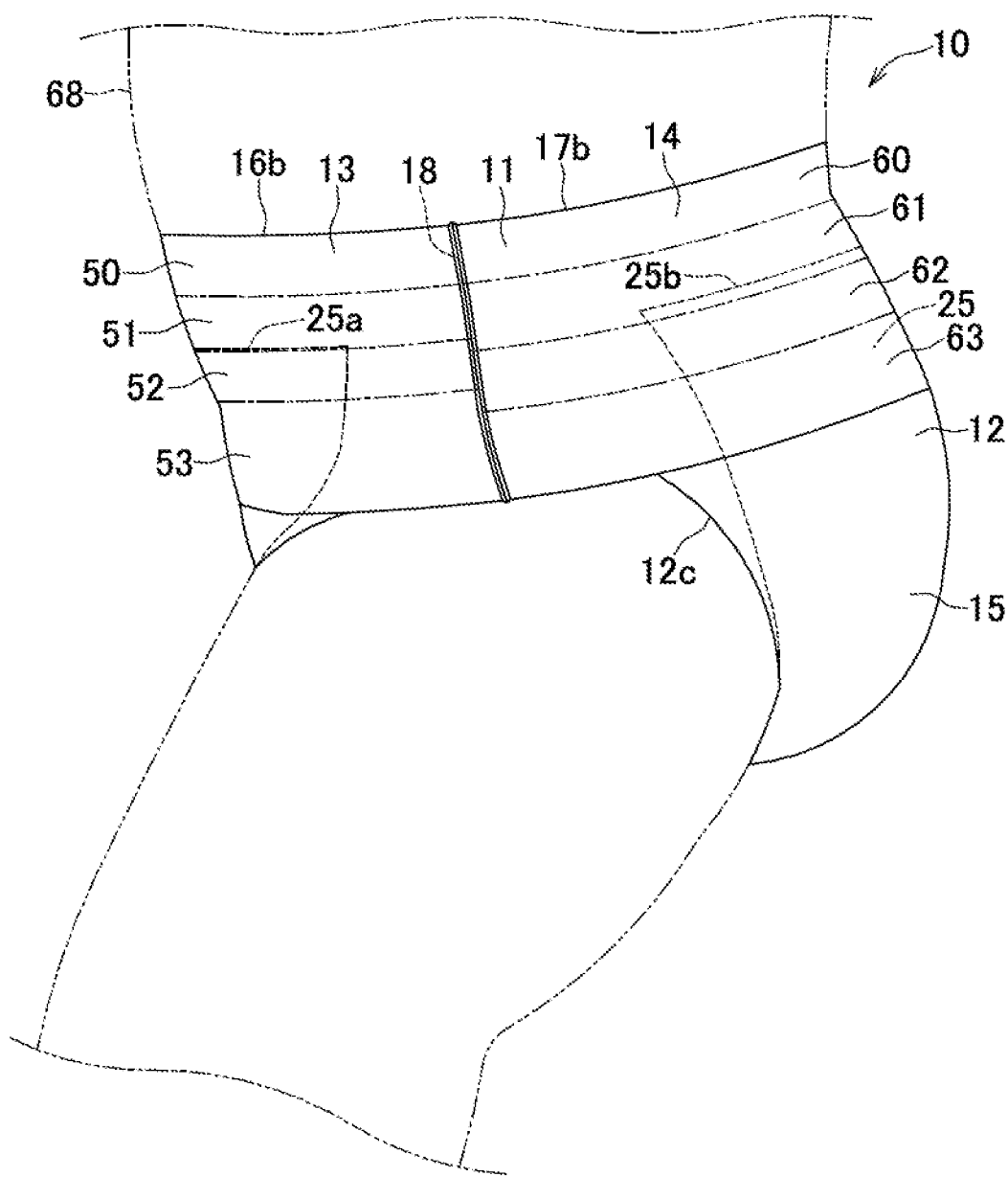
FIG. 7 is a side view showing how each elastic area is disposed in a worn state of the disposable diaper.

Referring to FIG. 7, in the worn state of the diaper 10, the outer elastic area 50 of the front waist elastic area and the outer elastic area 60 of the rear waist elastic area, the first intermediate elastic area 51 and the first intermediate elastic area 61, the second intermediate elastic area 52 and the second intermediate elastic area 62, the inner elastic area 53 and the inner elastic area 63, are positioned opposite to each other in the frontward-rearward direction. In the front waist elastic area and the rear waist elastic area, the tensile stress of the inner elastic areas 53, 63 being set to be the lowest, in a direction around the waist, the tensile stress of the elastic belt formed by the inner elastic areas 53, 63 is the minimum. In such manner, in the front and rear waist regions 13, 14, by setting the tensile stress of the inner elastic areas 53, 63 defining the leg opening edge to be the minimum, it is possible to avoid the movement of the thighs from being inhibited during walking.

<Method for Measuring Tensile Stress of Elastic Area>

For measurement of the tensile stress of each elastic area, Autograph type tensile tester (such as AG-1KN1) manufactured by Shimadzu Seisakusho Co., Ltd. was used. First, after having measured dimensions (K1, K2) in the lateral direction between inner edges of the side seam 18 in the front and rear waist regions 13, 14 in advance in a state of the diaper 10 elongated to the extent such that gathers by contraction effect of each elastic disappeared from a front surface thereof, both side edge portions including the side seams 18 of the diaper 10 were cut by a cutter, and the elastic areas 50 to 53, and 60 to 63 were cut out from a portion on the front waist region 13 side to the rear waist region 14 side, and let to be samples (a total of eight samples). Next, one end of each sample was pinched in a fixed chuck and the other end thereof was pinched in a movable chuck, and upon turning over after elongating to approximately 90% size of the initial dimensions K1, K2 at a velocity of 300 mm/min, a tensile load (N) when made to contract to 75% size of the initial dimensions K1, K2 was calculated, and a value converted to a stress value (N/mm) per unit width (mm) was let to be the tensile stress.

Second Embodiment

Figure 8:
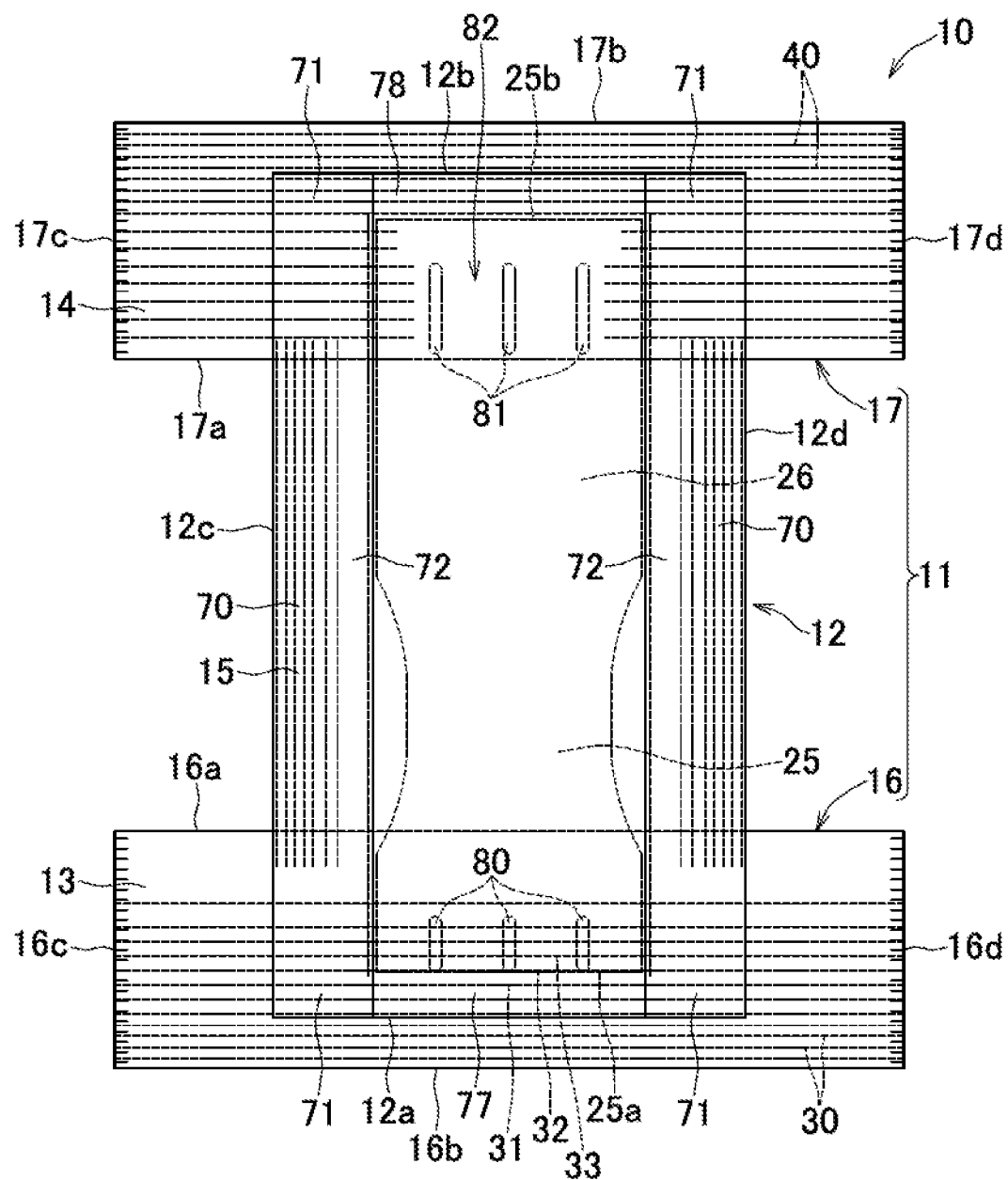
FIG. 8 is a plan view of an unfolded disposable diaper according to a second embodiment.

FIG. 8 is a plan view of the unfolded disposable diaper 10 according to a second embodiment. A basic configuration of the diaper 10 according to the present embodiment is similar to that of the first embodiment, and an arrangement differing from that in the first embodiment will be described below.

Referring to FIG. 8, in the present embodiment, a plurality of deformation guiding parts 80, 81 extending in the vertical direction is formed in the front and rear end parts of the liquid absorbent core 25. The deformation guiding part 80 may be a linear part positioned at a given spaced-apart dimension from each other in the lateral direction X, and may be a groove which is concave from the skin facing surface to the non-skin facing surface formed by compressing or removing a portion of the liquid absorbent core 25, or may be a slot in which the liquid absorbent core 25 does not exist. At a middle part of the rear waist region 14, by cutting and removing a portion of the rear waist elastic 40 positioned in the second intermediate elastic area 62 and the inner elastic area 63, an inelastic area 82 positioned to be overlapping with the rear end part of the liquid absorbent core 25 is defined.

The deformation guiding part 80 positioned at the front end part of the liquid absorbent core 25 extends from the frontend edge 25a toward the crotch region 15. By the plurality of front waist elastic members 30 including the third elastic member 33 of the second intermediate elastic area 52 intersecting the deformation guiding part 80, since a width dimension of the front end part of the liquid absorbent core 25 is shortened and also a portion positioned between the deformation guiding part 80 is curved along the abdomen, and even when the wearer changes the posture from a standing position to a seated position, the liquid absorbent core 25 does not press the abdomen along the shape of the body. On the other hand, in the rear waist region, the deformation guiding part 81 is positioned to be spaced apart inboard from the rear end edge 25b of the liquid absorbent core 25 in the vertical direction Y. Moreover, although the deformation guiding part 81 is disposed in the inelastic area 82, and the rear-end part of the liquid absorbent core 25 is not deformed directly due to contractile force of the rear waist elastic member 40 intersecting, by the deformation guiding part 81 being formed at the rear end part, it is susceptible to be deformed to be curved along roundness of the buttocks.

For each of the components forming the diaper 10, other than the materials described in the present description, various known materials generally used in this type of articles may be used without restrictions. Moreover, the terms such as 'the first', 'the second', and 'the third' used in the description and claims of the present invention are used simply for distinguishing similar components and positions.

The invention claimed is:

1. A disposable wearing article having a vertical direction and a lateral direction, comprising:
   a front waist region;
   a rear waist region;
   a crotch region extending between the front waist region and the rear waist region; and
   an absorbent panel having a liquid absorbent core extending to the front waist region and the rear waist region centering on the crotch region, wherein
   a plurality of linear front waist elastic member contractible in the lateral direction is disposed in the front waist region,
   the front waist elastic members include a first elastic member positioned adjacent to an outer side of a front end edge of the liquid absorbent core in the vertical direction, a second elastic member positioned adjacent to an inner side in the vertical direction of the front end edge, and a third elastic member positioned adjacent to an inner side in the vertical direction of the second elastic member,
   a contractile force of the first elastic and the second elastic members is weaker than a contractile force of the third elastic member, and
   in the front waist elastics of the front waist region, an elongation rate of the first elastic member is lower than an elongation rate of the second elastic member and the third elastic member.

2. The disposable wearing article according to claim 1, wherein the tensile stress of the outer elastic area of the rear waist region is higher than a tensile stress of the outer elastic area of the front waist region.

3. The disposable wearing article according to claim 1, further comprising:
   a pair of leakage barrier cuffs extending in the vertical direction on a skin facing side of the absorbent panel, wherein the leakage barrier cuff has both end fixing parts opposite in the vertical direction, both side parts extending in the vertical direction, and a free edge part in which a plurality of cuff elastic members extending in the vertical direction is disposed, and both end fixing parts are fixed at the front end edge and the rear end edge of the absorbent panel.

4. The disposable wearing article according to claim 1, wherein a deformation guiding part extending inward in the vertical direction from the front end edge is formed in the liquid absorbent core.

5. A disposable wearing article having a vertical direction and a lateral direction, comprising:
- a front waist region;
- a rear waist region;
- a crotch region extending between the front waist region and the rear waist region; and
- an absorbent panel having a liquid absorbent core extending to the front waist region and the rear waist region centering on the crotch region, wherein
- a plurality of linear front waist elastic member contractible in the lateral direction is disposed in the front waist region,
- the front waist elastic members include a first elastic member positioned adjacent to an outer side of a front end edge of the liquid absorbent core in the vertical direction, a second elastic member positioned adjacent to an inner side in the vertical direction of the front end edge, and a third elastic member positioned adjacent to an inner side in the vertical direction of the second elastic member,
- a contractile force of the first elastic and the second elastic members is weaker than a contractile force of the third elastic member,
- the front waist region includes an inner end edge, an outer edge end, an outer elastic area positioned on the inner end edge side, a first intermediate elastic area adjacent to an inner side of the outer elastic area in the vertical direction, including the first elastic member and the second elastic member, a second intermediate elastic area positioned between the first intermediate elastic area and the inner elastic area, including the third elastic member, and a tensile stress of the first intermediate elastic area is higher than a tensile stress of the outer elastic area, and
- for the front waist region, a correlation of tensile stress of elastic regions is a tensile stress of the second intermediate elastic area>a tensile stress of the first intermediate area≥a tensile stress of the outer elastic area>a tensile stress of the inner elastic area.

6. The disposable wearing article according to claim 5, wherein a contractile force of elastic members in the first intermediate elastic area, excluding the first elastic member and the second elastic member, is stronger than a contractile force of the first elastic member and the second elastic member.

7. The disposable wearing article according to claim 5, wherein the first intermediate elastic area of the front waist region overlaps in a planar view with the front end edge positioned outboard of the front end edge of the liquid absorbent core in the absorbent panel in the vertical direction.

* * * * *